(12) United States Patent
Murdoch

(10) Patent No.: US 6,723,873 B1
(45) Date of Patent: Apr. 20, 2004

(54) PRODUCTION OF TEREPHTHALIC ACID AND ETHYLENE GLYCOL FROM POLYETHLENE TEREPHTHALATE BY AMMONIOLYSIS

(75) Inventor: William Speight Murdoch, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 142 days.

(21) Appl. No.: 09/651,161

(22) Filed: Aug. 30, 2000

(51) Int. Cl.[7] .............................................. C07C 51/42

(52) U.S. Cl. ....................... 562/485; 562/480; 562/486; 562/487; 521/48

(58) Field of Search ................................ 562/480, 485, 562/486, 487; 521/48

(56) References Cited

U.S. PATENT DOCUMENTS

| | | | |
|---|---|---|---|
| 3,624,049 A | * | 11/1971 | Ventura et al. |
| 3,849,489 A | | 11/1974 | Rudzki |
| 3,968,152 A | * | 7/1976 | Sze et al. |
| 4,542,239 A | | 9/1985 | Lamparter |
| 5,210,292 A | | 5/1993 | Park |

* cited by examiner

Primary Examiner—Johann Richter
Assistant Examiner—Paul A. Zucker
(74) Attorney, Agent, or Firm—Susan F. Johnston; Dennis V. Carmen

(57) ABSTRACT

A process for forming reactants useful in the manufacture of polyethylene terephthalate includes the steps of: (a) contacting recyclable polyethylene terephthalate with ammonium hydroxide whereby a mixture of ammonium terephthalate and ethylene glycol is formed, (b) separating the ammonium terephthalate, and (c) heating said ammonium terephthalate at a temperature from about 225° C. to about 300° C. to produce terephthalic acid.

14 Claims, 1 Drawing Sheet

PRODUCTION OF TEREPHTHALIC ACID AND ETHYLENE GLYCOL FROM POLYETHLENE TEREPHTHALATE BY AMMONIOLYSIS

FIELD OF THE INVENTION

The present invention relates to the field of depolymerization and purification of recyclable polyethylene terephthalate. More specifically, the present invention relates to ammoniolysis depolymerization of polyethylene terephthalate to form terephthalic acid and ethylene glycol, which may be used as starting materials in the production of a recycled polyethylene terephthalate product.

BACKGROUND OF THE INVENTION

It is increasingly important to provide economically feasible processes for recycling waste. One such waste is recyclable polyethylene terephthalate (PET). "Recyclable PET" includes PET that is contaminated with a material present on the polymer surface or diffused into the polymer, PET that is copolymerized with modifying agents, PET that is formed into an article containing layers or coatings of other materials, and scrap PET produced during various molding, film, and fiber production processes. Much recyclable PET is contaminated to the extent that it must be depolymerized and purified prior to being recycled for use as food packaging. Common contaminants include colorants and dyes, opacifiers, polymerization catalyst metals, polymer modifiers, barrier resins, and oxygen absorbers. The predominant source of recyclable PET is discarded PET soft drink bottles. Scrap PET fiber, scrap PET film, and poor quality PET polymer are also major sources of recyclable PET.

PET is commercially manufactured from ethylene glycol (EG) and either dimethyl terephthalate (DMT) or terephthalic acid (TPA). The DMT route was the first commercialized, but for economic reasons, all modern PET manufacturing plants use the TPA route. It is known that methanol may be used to depolymerize PET to form DMT. As noted above, the DMT must be converted either to TPA by hydrolysis or to polyester monomer by reaction with EG before it can be used in a TPA-based PET production process. The cost of these conversions and the necessary purification steps is high. In light of the above, it would be desirable to provide a depolymerization and purification process wherein the TPA and ethylene glycol monomers for use in the production of a new PET product are directly formed during depolymerization of recyclable PET.

TPA can be made from recyclable PET by neutral hydrolysis using water, but this is not economically attractive because of the high temperature and pressure required and because of the difficulty of purifying the resulting TPA.

TPA can be made from recyclable PET by saponification of PET using sodium or potassium hydroxide. The resulting sodium or potassium terephthalate salt is converted to TPA using a strong mineral acid, such as sulfuric acid. This method is deleterious in that the sodium or potassium hydroxide and the required mineral acid are expensive. Additionally, the salt byproduct formed has little economic value. Accordingly, such known saponification processes for the production of EG and TPA from PET are economically unattractive.

U.S. Pat. No. 4,542,239 discloses a process for recovering terephthalic acid from waste polyethylene terephthalate by ammoniolysis. PET is reacted with ammonium hydroxide to form diammonium terephthalate and ethylene glycol. The diammonium terephthalate is converted to TPA using sulfuric acid, thereby producing an ammonium sulfate salt. While the ammonia may be recovered from the salt for reuse in the process by the addition of a base, such as calcium hydroxide, the process produces a nearly valueless gypsum byproduct and consumes valuable sulfuric acid and calcium hydroxide.

Accordingly, there is a need for a new process for directly forming TPA from recyclable PET.

SUMMARY OF THE INVENTION

The present invention is a process of forming reactants useful in the manufacture of polyethylene terephthalate that comprises the steps of: (a) treating recyclable PET with ammonium hydroxide whereby a mixture of ammonium terephthalate and EG is formed, and (b) heating the ammonium terephthalate so formed at a temperature of from about 225° to about 300° C. whereby TPA and ammonia are formed. The present process preferably further comprises a step of polymerizing the EG and the TPA so formed under esterification and polycondensation conditions whereby a PET product is formed.

DETAILED DESCRIPTION

Figure 1:
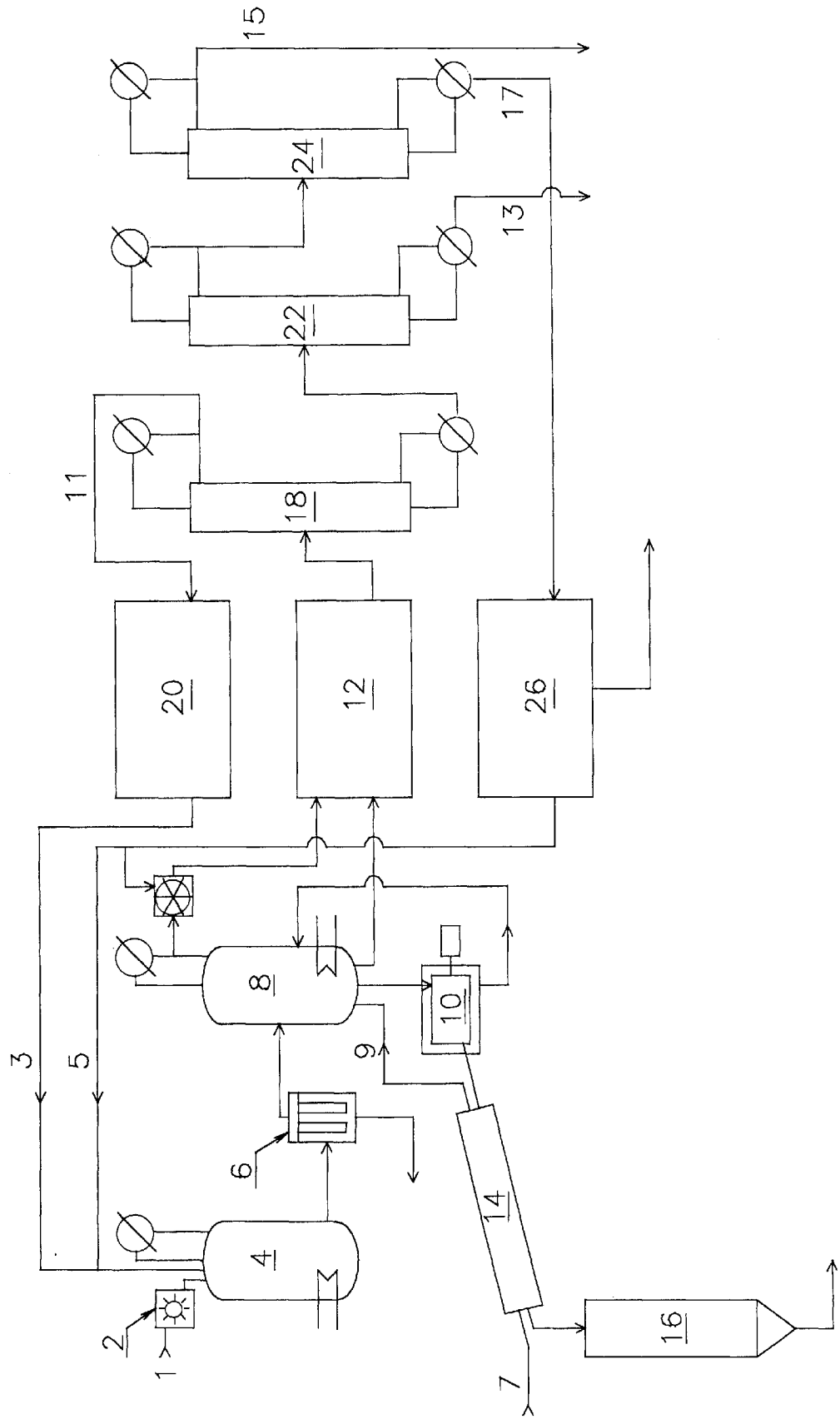
FIG. 1 schematically illustrates a preferred embodiment of the process of the present invention.

In the process of the present invention, the reactants useful in the manufacture of PET, TPA and EG are formed in a three step process. In the first step, recyclable PET is treated with ammonium hydroxide to form a mixture of mono- and diammonium terephthalate (the mixture is referred to hereinafter as ammonium terephthalate) dissolved along with any excess ammonia in EG and water. Second, the ammonium terephthalate is removed from the mixture, preferably by crystallization of the ammonium terephthalate and evaporation of the ammonia, EG, and water. Third, the ammonium terephthalate is heated at a temperature sufficient to release ammonia to produce TPA. The present process optionally includes step of recovering the ammonia, EG, and water for reuse.

It has unexpectedly been found that depolymerizing PET by ammoniolysis using ammonium hydroxide provides a reaction mixture from which TPA is easily and directly formed. TPA is advantageously produced from the reaction mixture, without the addition of any other substance, using heat alone. The formation of TPA occurs in the essential absence of acids such as sulfuric acid, at a pH greater than about 4.0.

The recyclable PET used in the present invention is selected from PET homopolymer and PET copolymer. The recyclable PET preferably contains repeat units having a dicarboxylic acid component from preferably at least about 50 mole percent and more preferably at least about 75 mole percent TPA and a diol component from preferably at least about 50 mole percent EG, more preferably at least about 75 mole percent EG, based upon 100 mole percent dicarboxylic acid and 100 mole percent diol present in the recyclable PET.

In the recyclable PET copolymer, the dicarboxylic acid component of the PET may optionally be modified with up to about 50 mole percent, and preferably up to about 25 mole percent of one or more different dicarboxylic acids. Such additional dicarboxylic acids include aromatic dicarboxylic acids preferably having 8 to 14 carbon atoms, aliphatic dicarboxylic acids preferably having 4 to 12 carbon atoms, or cycloaliphatic dicarboxylic acids preferably having 8 to 12 carbon atoms. Examples of dicarboxylic acids to be included with TPA are: phthalic acid, isophthalic acid, naphthalene-2,6-dicarboxylic acid, cyclohexanedicarboxylic acid, cyclohexanediacetic acid, diphenyl-4,4'-dicarboxylic acid, succinic acid, glutaric acid, adipic acid, azelaic acid, sebacic acid, and the like.

In addition, the glycol component of the recyclable PET copolymer may optionally be modified with up to about 50 mole percent and preferably up to about 25 mole percent, of one or more different diols other than EG. Such additional diols include cycloaliphatic diols preferably having 6 to 20 carbon atoms or aliphatic diols preferably having 3 to 20 carbon atoms. Examples of such diols to be included with ethylene glycol are 1,4-cyclohexanedimethanol, propane-1,3-diol, butane-1,4-diol, pentane-1,5-diol, hexane-1,6-diol, 3-methylpentanediol-(2,4), 2-methylpentanediol-(1,4), 2,2,4-trimethylpentane-diol-(1,3), 2-ethylhexanediol-(1,3), 2,2-diethylpropanediol-(1,3), hexanediol-(1,3), 1,4-di-(hydroxyethoxy)-benzene, 2,2-bis-(4-hydroxycyclohexyl)-propane, 2,4-dihydroxy-1,1,3,3-tetramethylcyclobutane, 2,2-bis(3-hydroxyethoxyphenyl)-propane, and 2,2-bis-(4-hydroxypropoxyphenyl)-propane. The 1,4-cyclohexanedimethanol may be in the cis or the trans form or as cis/trans mixtures.

The recyclable PET resin may also contain small amounts of trifunctional or tetrafunctional comonomers such as trimellitic anhydride, trimethylolpropane, pyromellitic dianhydride, pentaerythritol, and other polyester forming polyacids or polyols generally known in the art.

The recyclable PET may additionally be blended with up to 50 mole percent, preferably up to 25 mole percent of another polyester, and any other polymer that does not interfere with the intended reactions of the present process.

In the process of the present invention, the recyclable PET is contacted with ammonium hydroxide in an aqueous medium to produce a solution of mono and diammonium terephthalates dissolved in a mixture of EG, water and excess ammonia. Scrap PET is introduced into the ammoniolysis reactor after being first comminuted (by grinding or the like) into a particle size suitable for pumping as part of an aqueous slurry. The concentration of ammonium hydroxide added to the reactor may range from about 100 to about 300 molar percent the PET. The concentration of the ammonium hydroxide solution should be strong enough to give a suitably fast reaction rate but dilute enough to allow all of the ammonium terephthalate formed to dissolve in the water so that the resulting mixture may be filtered. Suitable concentrations range from about 10 to about 35% ammonia by weight with concentrations between about 20 and about 35% being preferable. Temperatures of about 160 to about 290° C. are suitable for the ammoniolysis reaction, with a temperature between about 190 and about 230° C. being preferable. The ammoniolysis reaction should be conducted under an elevated pressure that is sufficient to cleave the PET ester linkage, prevent the escape of ammonia, and promote formation of ammonium terephthalate. Suitable pressures range from about 13 to about 70 bar gauge for temperatures above about 200° C., and from about 6 to about 30 bar gauge for temperatures below 200° C. Under the preferred conditions the ammoniolysis of PET occurs in from about 5 to about 45 minutes. The ammoniolysis step of the present process is described in greater detail in U.S. Pat. No. 4,542,239, the disclosure of which is incorporated herein in it's entirety, which also describes the use of oxidizing conditions during the ammoniolysis to destroy certain types of contaminants which may be present in the recyclable PET fed to the process. It is preferable to add a sufficient amount of EG during ammoniolysis to wet all of the PET solids in the reactor and fill the void spaces between the PET particles. The presence of such additional amount of EG advantageously lowers the vapor pressure of the materials in the reactor, thereby allowing operation at lower pressures and reducing the cost of the reactor system.

The second step of the present process includes heating the mono and diammonium terephthalate sufficiently to evaporate the excess ammonia, water, and ethylene glycol from the mixture in a crystallizer. The resulting slurry is centrifuged or filtered to separate the solid ammonium terephthalate from the remaining liquid. The liquid is returned to the crystallizer for further evaporation, and the solid ammonium terephthalate filtrate cake is fed to a kiln where it is decomposed in the presence of steam to produce ammonia and TPA. When essentially all of the ammonium terephthalate has been removed from the liquid, the remaining mother liquor is preferably removed for recovery of any remaining EG.

The temperature in the crystallizer must remain below the decomposition temperature of the ammonium terephthalate. Further, the condensing temperature of the vapors leaving the crystallizer should not be so low as to require an expensive refrigerated condenser. Accordingly, the evaporation temperature should be between about 100 and about 250° C. and most preferably between about 140 and about 210° C. The pressure may range from about 150 millibar absolute to about 3 bar gauge, but it is preferable to operate the evaporator at a pressure between about 500 millibar absolute and about 1.5 bar gauge.

The third step of heating the ammonium terephthalate to form terephthalic acid and ammonia is preferably conducted in a kiln operating at temperatures between about 225 and about 300° C. and preferably between about 260 and about 290° C. At lower temperatures, the decomposition is too slow and lower boiling small contaminants such as p-toluic acid and terephthaldehyde remain present. At higher temperatures the sublimation of the TPA into the vapor phase becomes appreciable. While the process may be operated under pressure or under vacuum, atmospheric operation is preferred since equipment costs are lower. The presence of steam (water) in the kiln vapor space during heating is beneficial and highly preferable since steam retards the undesirable decomposition of diammonium terephthalate to ammonium terephthalamate and similar compounds. The weight of steam fed to the kiln is up to twice the weight of the TPA produced, with an amount between about 50 to about 100 weight percent of TPA being preferred. The dry TPA produced in the kiln is suitable for use in the manufacture of PET.

In a preferred embodiment of the present invention, an optional fourth step of the process of the present invention includes recovering the ammonia, ethylene glycol, and water for recycling and reuse in the process. Ammonia, water, and ethylene glycol evaporated from the ammonium terephthalate slurry in the crystallizer; steam and ammonia removed from the kiln; and spent liquor from the crystallizer may be combined in a storage tank and then separated by distillation into ammonium hydroxide, ethylene glycol, and waste by distillation. This separation can be conveniently accomplished in three distillations.

In the first distillation, ammonia is removed from the ammonia-water-glycol mixture. This distillation column is operated with a bottom temperature sufficiently high enough to ensure that little or no ammonia remains in the bottom product. The top temperature is selected such that all of the ammonia and part of the water passes over the top of the column. This top temperature is preferably selected so that the ammonia-water mixture produced by this column is of the same composition as the ammonium hydroxide solution used in the ammoniolysis step of the process. While this distillation could be accomplished at pressures both below and above atmospheric, for simplicity it is best performed at atmospheric pressure.

The second distillation removes both materials which are nonvolatile and materials with boiling points higher than ethylene glycol. This column is operated with a bottom temperature sufficiently high so that no significant amount of ethylene glycol leaves in the bottom product. The top temperature is held sufficiently low so that little material with a boiling point higher than ethylene glycol leaves the top of the column. The bottom product from this column is a waste stream composed of diethylene glycol, catalysts, and additives that were present in the recyclable PET, and small amounts of terephthalic acid, ammonium terephthalamate, terephthalamic acid, and related compounds. The top product from the distillation is water and ethylene glycol with small amounts of materials with boiling points between water and ethylene glycol, primarily 1,4 dioxane. While this distillation could be accomplished at pressures both below and above atmospheric, for simplicity it is best performed at atmospheric pressure. The third distillation removes as a waste stream the water and intermediate boiling compounds from the top product of the second distillation leaving as a remainder ethylene glycol of a purity suitable for reuse in the manufacture of polyester. The bottom temperature of this column is selected so that little or no water remains in the ethylene glycol bottom product. The top temperature is selected so that little or no ethylene glycol leaves the column with the wastewater stream.

FIG. 1 schematically illustrates a preferred embodiment of the preferred four step process of the present invention. The process shown in FIG. 1 utilizes a combination of batch reaction equipment and continuous distillation equipment. However, the process can be equally well accomplished using only batchwise steps or using only continuous process steps.

PET flake is added at process line 1. If the incoming PET flake is of a low bulk density, it is ground to a powder in grinder 2 to increase its bulk density. PET powder is charged to the ammoniolysis reactor 4 along with EG from line 3 and ammonium hydroxide from line 5. The reactor 4 is preferably equipped with stirring means for continuously stirring the reaction mixture to accelerate the dissolution of the PET. The PET is converted to diammonium terephthalate and EG which are dissolved in water along with any excess ammonia. The liquid mixture is filtered through filter 6 to remove contaminating solids prior to the mixture being transferred to the crystallizer 8. In the crystalizer the excess ammonia, water, and EG are recovered and the diammonium terephthalate is crystallized to a slurry containing mono and diammonium terephthalate. The crystals are removed using a centrifuge 10 or any other solids separation method known to those skilled in the art and the liquor returned to the crystallizer 8 for further evaporation. After the liquor is exhausted, it is pumped to the liquid storage tank 12. The mono and diammonium terephthalate crystals from the centrifuge 10 pass to a kiln 14 where heat and steam 7 convert the mono and diammonium terephthalate to TPA. The TPA is accumulated in a storage silo 16. The steam and resulting ammonia return to the crystallizer through line 9 where the steam provides part of the needed heat and where the ammonia can be recovered in the product from the condenser.

FIG. 1 further illustrates that the separation of the material stored in the liquid storage tank 12 is separated via the continuous distillation train of columns 18, 22, and 24. Ammonium hydroxide is removed by the first column 18 and sent to storage 20 via line 11 as an ammonia-water mixture. The second column 22 removes the high boiling point and non-volatile materials as waste stream 13. In the third column 24, the water and glycol are separated. The EG is sent to its storage tank 26 and the waste water is sewered through line 15. The top product steam from this third column could supply the steam to the kiln 14.

It will be appreciated that the present process produces TPA and EG from recyclable PET, with the TPA and EG being suitable feedstock for a modern PET manufacturing plant. It is beneficial that the process has no byproducts, requires only reagents that may be later recovered in the process, and produces only small amounts of waste.

The process of the present invention is most advantageously combined with the further fifth step of forming a recycled PET-containing product by reacting the EG formed during the ammoniolysis step with the TPA formed during the step of heating the diammonium terephthalate to produce a 100% recycle content PET product. This polymerization generally occurs at a temperature between about 100 to 300° C. and a pressure of about 0 to about 6 bar. Additionally, new EG and TPA can be included in this reaction to produce a PET product with any proportion of recycle content. In the PET formation step, the EG and the TPA are reacted together to form PET, and the presence of TPA or EG made from recyclable PET has no effect on the PET formation process. The concentration of EG in the polymerization step is about 100 to about 200 molar percent of the TPA.

The production of PET from TPA and EG, the conditions, equipment, and catalysts employed is well known to those skilled in the art. The generally known three-stage polyesterification processes are suitable for use as part of the process of the present invention and include the esterification stage, the prepolymer stage, and the polycondensation stage. The basic conditions which define these three stages are set out below.

The esterification and prepolymer conditions required for the present process are well known in the polymers art. Generally, dicarboxylic acid is reacted with diol to form esters and water. The TPA and EG formed in the present process may be used alone or reacted with new acids and glycols to form a homopolyester or heteropolyester having any percentage of recycled content. The water formed is removed from the reaction mixture by distillation using a partial condenser operated at a temperature above the boiling point of water yet below the boiling point of the solvent so that the solvent is refluxed back into the reaction mixture. The solvent used in the esterification reaction of the present process can be any suitable organic solvent having a boiling point of about 100 to 250° C., preferably about 140 to 210° C. It is preferable to use excess reactant glycol as the solvent. EG is preferred, having a boiling point of about 198° C.

The esterification reaction of the process of the present invention is performed under atmospheric pressure or elevated pressures of about 0 to 6 bar, preferably about 0 to 2 bar, at a temperature of from above the boiling point of water to about 300° C. The degree of polymerization for this stage is about 1 to 5.

In the esterification stage of the melt-phase process, a mixture of polyester monomer (diglycol esters of dicarboxylic acids) and oligomers are produced by conventional, well-known processes. The esterification reaction is conducted at a temperature between about 220° C. to about 270° C. and a pressure of about 0 to about 2 bar in the presence or absence of suitable esterification catalysts such as acids or titanium suitable forms of which are generally known in the art. The catalysts can be used alone or in combination. Preferably, the total amount of catalyst is less than about 100 ppm on an elemental basis. Suitable colorants may also be added at this point. The reaction is conducted for about 1 to about 4 hours. It should be understood that generally the lower the reaction temperature, the longer the reaction will have to be conducted.

Generally, at the end of esterification, a polycondensation catalyst is added. Suitable polycondensation catalysts include salts of titanium, gallium, germanium, tin, antimony and lead, preferably antimony or germanium or a mixture thereof Preferably the amount of catalyst added is between about 90 and about 250 ppm when germanium or antimony is used. Suitable forms such as, but not limited to antimony oxide are well known in the art. The prepolymer reaction is conducted at a temperature less than about 280° C. and preferably between about 240° C. and about 280° C. at a pressure sufficient to aid in removing undesirable reaction products such as EG. The monomer and oligomer mixture is typically produced continuously in a series of one or more reactors operating at elevated temperatures and pressures at one atmosphere or greater. Alternately, the monomer and oligomer mixture could be produced in one or more batch reactors.

Next, the mixture of polyester monomer and oligomers undergoes melt-phase polycondensation to produce a low molecular weight precursor polymer. The precursor is produced in a series of one or more reactors operating at elevated temperatures. Temperatures for this step are generally between about 240° C. to about 290° C. and a pressure between about 0 and 2 mm Hg. Once the desired inherent viscosity is reached, the PET polymer is pelletized.

In the drawings and specification, there have been disclosed typical preferred embodiments of the invention and, although specific terms are employed, they are used in a generic and descriptive sense only, and not for purposes of limitation. The scope of the invention is set forth in the following claims.

I claim:

1. A process for recycling polyethylene terephthalate to form reactants useful in the manufacture thereof comprising:
   (a) contacting recyclable polyethylene terephthalate with ammonium hydroxide to form a mixture of ammonium terephthalate and ethylene glycol;
   (b) separating said ammonium terephthalate from the mixture; and
   (c) heating said ammonium terephthalate to form TPA and ammonia.

2. The process of claim 1 wherein the concentration of ammonium hydroxide is from about 100 to about 300 molar percent of said recyclable polyethylene terephthalate.

3. The process of claim 1 wherein step (a) is conducted at a temperature of about 160° C. to about 290° C., and a pressure sufficient to prevent the escape of ammonia from said mixture, and step (c) is conducted at a temperature of about 225° C. to about 300° C.

4. The process of claim 1 wherein said removing of said ammonium terephthalate from the mixture is conducted using evaporation and crystallization or centrifugation.

5. The process of claim 1 further comprising reacting the ammonia formed in said heating step with water to form a portion of the ammonium hydroxide used in said step (a).

6. The process of claim 1 wherein said heating step is conducted in the presence of steam.

7. The process of claim 1 wherein said step (c) is conducted at a pH greater than about 4.0.

8. A polyethylene terephthalate depolymerization and purification process comprising:
   (a) conducting depolymerization by treating recyclable polyethylene terephthalate with ammonium hydroxide to form a mixture of ammonium terephthalate and ethylene glycol;
   (b) removing said ammonium terephthalate from the mixture;
   (c) heating said ammonium terephthalate to form terephthalic acid and ammonia; and
   (d) polymerizing said ethylene glycol and said terephthalic acid under esterificatlon and polycondensation conditions to form a polyethylene terephthalate product.

9. The process of claim 8 wherein the concentration of ammonium hydroxide in said depolymization step is from about 100 to about 300 molar percent of said recyclable polyethylene terephthalate, and the concentration of ethylene glycol in said polymerizing step is from about 100 to about 200 times molar percent of said terephthalic acid.

10. The process of claim 8 wherein said depolymerization step is conducted at a temperature of about 160° C. to about 290° C. under a pressure sufficient to prevent the escape of ammonia from said mixture, said heating step is conducted at a temperature of about 225° C. to about 300° C., and said polymerizing step is conducted at temperatures between about 100° C. and about 300° C. and at pressures between 0 to about 6.

11. The process of claim 8 wherein said removal of said ammonium terephthalate from the mixture is conducted through crystallization and evaporation.

12. The process of claim 8 comprising reacting the ammonia formed in said heating step with water to form the ammonium hydroxide used in said depolymerization.

13. The process of claim 8 wherein said heating step is conducted in the presence of steam.

14. The process of claim 8 wherein said heating step is conducted in the essential absence of an acid.

* * * * *